(12) United States Patent
Firoozabadi et al.

(10) Patent No.: US 10,076,670 B2
(45) Date of Patent: Sep. 18, 2018

(54) CONSISTENCY MONITORING FOR ECG SHOCK ADVISORY DECISIONS

(71) Applicant: KONINKLIJKE PHILIPS N.V., Eindhoven (NL)

(72) Inventors: Reza Firoozabadi, Thousand Oaks, CA (US); Saeed Babaeozadej, Arlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 52 days.

(21) Appl. No.: 15/109,507

(22) PCT Filed: Dec. 24, 2014

(86) PCT No.: PCT/IB2014/067312
§ 371 (c)(1),
(2) Date: Jul. 1, 2016

(87) PCT Pub. No.: WO2015/101911
PCT Pub. Date: Jul. 9, 2015

(65) Prior Publication Data
US 2016/0331984 A1    Nov. 17, 2016

Related U.S. Application Data

(60) Provisional application No. 61/922,887, filed on Jan. 2, 2014.

(51) Int. Cl.
*A61N 1/39* (2006.01)
*A61B 5/04* (2006.01)
(Continued)

(52) U.S. Cl.
CPC .......... *A61N 1/3925* (2013.01); *A61B 5/0404* (2013.01); *A61B 5/046* (2013.01); *A61B 5/04012* (2013.01); *A61B 5/4836* (2013.01); *A61N 1/3931* (2013.01); *A61N 1/3993* (2013.01)

(58) Field of Classification Search
None
See application file for complete search history.

(56) References Cited

U.S. PATENT DOCUMENTS 6,108,578 A * 8/2000 Bardy ...................... A61N 1/39
607/30
6,141,584 A * 10/2000 Rockwell ................ A61N 1/39
128/903

(Continued)

FOREIGN PATENT DOCUMENTS

WO    2013179234 A1    3/2009

*Primary Examiner* — Brian T Gedeon

(57) ABSTRACT

A defibrillator or other patient monitoring device (20) employing an ECG monitor (23) and a controller (25). The ECG monitor (23) monitors an ECG waveform of a heart of a patient. The controller (25) segments the ECG waveform, and for each ECG waveform segment of a series of ECG waveform segments, generates an ECG shock advisory between a shock decision, a no-shock decision and an optional shock indecision. The controller (25) further monitors a consistency of the ECG shock advisories between consistent shock decisions, consistent no-shock decisions, and optional inconsistent shock decisions.

20 Claims, 15 Drawing Sheets

(51) Int. Cl.
  *A61B 5/00* (2006.01)
  *A61B 5/0404* (2006.01)
  *A61B 5/046* (2006.01)

(56) References Cited

U.S. PATENT DOCUMENTS

| | | | | |
|---|---|---|---|---|
| 6,304,773 | B1* | 10/2001 | Taylor | A61N 1/39 600/515 |
| 6,694,187 | B1* | 2/2004 | Freeman | A61N 1/39 607/5 |
| 7,650,181 | B2* | 1/2010 | Freeman | A61H 31/00 600/484 |
| 9,308,383 | B2* | 4/2016 | Didon | A61N 1/39 |
| 9,409,034 | B2* | 8/2016 | Babaeizadeh | A61N 1/39 |
| 9,642,547 | B2* | 5/2017 | Tan | A61B 5/0464 |
| 2003/0060723 | A1* | 3/2003 | Joo | A61B 5/0535 600/510 |
| 2009/0063094 | A1 | 3/2009 | Burka et al. | |
| 2011/0082510 | A1 | 4/2011 | Sullivan | |
| 2011/0202101 | A1 | 8/2011 | Tan et al. | |
| 2013/0273624 | A1 | 10/2013 | Yukawa et al. | |
| 2013/0274624 | A1 | 10/2013 | Mahajan et al. | |
| 2013/0282072 | A1* | 10/2013 | Abdeen | A61N 1/39 607/7 |
| 2014/0107541 | A1* | 4/2014 | Sullivan | A61B 5/7217 601/41 |
| 2016/0015991 | A1 | 1/2016 | Firoozabadi et al. | |

* cited by examiner

CONSISTENCY MONITORING FOR ECG SHOCK ADVISORY DECISIONS

This application is a national stage application under 35 U.S.C. § 371 of International Application No. PCT/IB2014/067312 filed on Dec. 24, 2014 and published in the English language on Jul. 9, 2015 as International Publication No. WO/2015/101911, which claims priority to U.S. Application No. 61/922,887 filed on Jan. 2, 2014, the entire disclosures of which are incorporated herein by reference.

The present invention generally relates to electrocardiogram ("ECG") based shock advisory decisions made by a defibrillator or other patient monitoring device. The present invention specifically relates to increasing the accuracy of real-time shock advisory decisions, particularly during a cardiopulmonary resuscitation ("CPR") of sudden cardiac arrest patients.

Generally, the output of a real-time shock advisory method implemented in a defibrillator is based on analyzing sequential ECG segments during CPR and may be inaccurate for various reasons. Examples of such reasons include, but are not limited to, presence of artifacts in the ECG waveform, imperfect removal of chest compression artifact out of the ECG waveform if filtered, temporary cardiac rhythm changes, and invalid identification of an individual ECG segment.

More particularly, the shock advisory method generally provides a shock advice only for patients with some specific rhythms (e.g., ventricular fibrillation ("VF")). Delivering a shock is not advised for other types of rhythms (e.g., an asystole rhythm or a normal sinus rhythm). Generally, defibrillation is performed by a defibrillator, which analyzes the ECG of a patient to indicate if a shock is needed. An Automatic External Defibrillator ("AED") will automatically analyze the ECG of a patient to indicate if a shock is needed. Some shock advisory methods implemented in AEDs may not be significantly impacted by chest compressions ("CC"), but in most techniques, chest compressions must be interrupted during defibrillator rhythm analysis because the mechanical activity from the CC introduces artifacts into the ECG waveform that may often make the rhythm analysis of current ECG unreliable. Most proposed shock advisory methods rely on filtering the CC artifact to clean up the ECG waveform for the defibrillator.

Furthermore, some types of artifacts (e.g., motion artifact) may impact the rhythm analysis of ECG waveforms and result in either no usable output (artifact) or erroneous classification. Any temporary abnormality in the ECG waveform can affect the shock advisory decision suddenly and cause inconsistency in the series of shock advisory outputs. In addition, a filtering process in the shock advisory methods which filters the CC artifacts may impact the analysis. Specifically, no matter how good a filtering technique may be, there may be some residuals left on the ECG which could potentially lead to incorrect determination of the underlying rhythm by the defibrillator shock advisory method. During non-shockable rhythms, in particular asystole, such an imperfect filtration of the CC artifact may cause the shock advisory module to erroneously call the rhythm shockable because the residuals may look like VF to the module. On the other hand, for shockable rhythms such as VF, the filtering technique may mistakenly filter out some of the VF information which may consequently make the rhythm look non-shockable to the shock advisory module.

Known defibrillator shock advisory methods generally analyze one short segment of the ECG waveform (e.g., 4.5 seconds) at a time to classify it as either shockable, non-shockable, or artifact. Then, the defibrillator shock advisory method either relies on the most recent segment or the two (2) or three (3) recent segments to make the final advice to deliver the shock or not.

The present invention improves the accuracy of shock advisory by analyzing a series of ECG segments and intelligently combining the output for this series of ECG segments. The final shock advice (e.g., deliver shock, pause chest compression to get clean ECG, or continue chest compression) considers the trend and history of outputs for individual ECG segments and removes temporary invalid segment identifications.

One form of the present invention is a patient monitoring device, such as a defibrillator, employing an ECG monitor and a controller, such as a patient monitoring device and/or defibrillation controller. In operation, the ECG monitor monitors an ECG waveform of a heart of a patient and the controller segments the ECG waveform. For each ECG waveform segment of a series of ECG waveform segments, the controller generates an ECG shock advisory between a shock decision, a no-shock decision and an optional shock indecision, and further monitors a consistency of the ECG shock advisories between consistent shock decisions, consistent no-shock decisions, and optional inconsistent shock decisions.

From the monitoring of the consistency of the ECG shock advisories, the controller can generate and communicate a consistency shock advisory in real-time to a user of the defibrillator as a shock decision, a no-shock decision or an optional shock indecision.

Alternatively, the controller can generate a defibrillation shock advisory as a logical combination of the consistency shock advisory and one or more of the ECG shock advisories, and communicate the defibrillation shock advisory in real-time to a user of the defibrillator as a shock decision, a no-shock decision or an optional shock indecision.

Furthermore, the controller can generate a consistency shock indication of the consistency shock advisory that is communicated in real-time to the user of the defibrillator to facilitate the user in reacting to the ECG shock advisories.

A second form of the present invention is the aforementioned controller employing a shock advisor and a consistency advisor. The shock advisor segments the ECG waveform of the heart of the patient, and for each ECG waveform segment of the series of ECG waveform segments, the shock advisor generates the ECG shock advisory between the shock decision, the no-shock decision and the optional shock indecision. The consistency monitor monitors the consistency of the ECG shock advisories between the consistent shock decisions, the consistent no-shock decisions, and the optional inconsistent shock decisions.

A third form of the invention is a method of operating a patient monitoring device, such as a defibrillator. The method includes the defibrillator segmenting the ECG waveform of the heart of the patient, and for each ECG waveform segment of a series of ECG waveform segments, the defibrillator generating a shock advisory decision between the shock decision, the no-shock decision and the optional shock indecision. The method can further include the defibrillator determining a consistency of the shock advisory decisions between consistent shock decisions, consistent no-shock decisions, and optional inconsistent shock decisions.

The foregoing forms and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting the scope of the present invention being defined by the appended claims and equivalents thereof.

To facilitate an understanding of the present invention, exemplary embodiments of an automated external defibrillator of the present invention will be provided herein.

Figure 1:
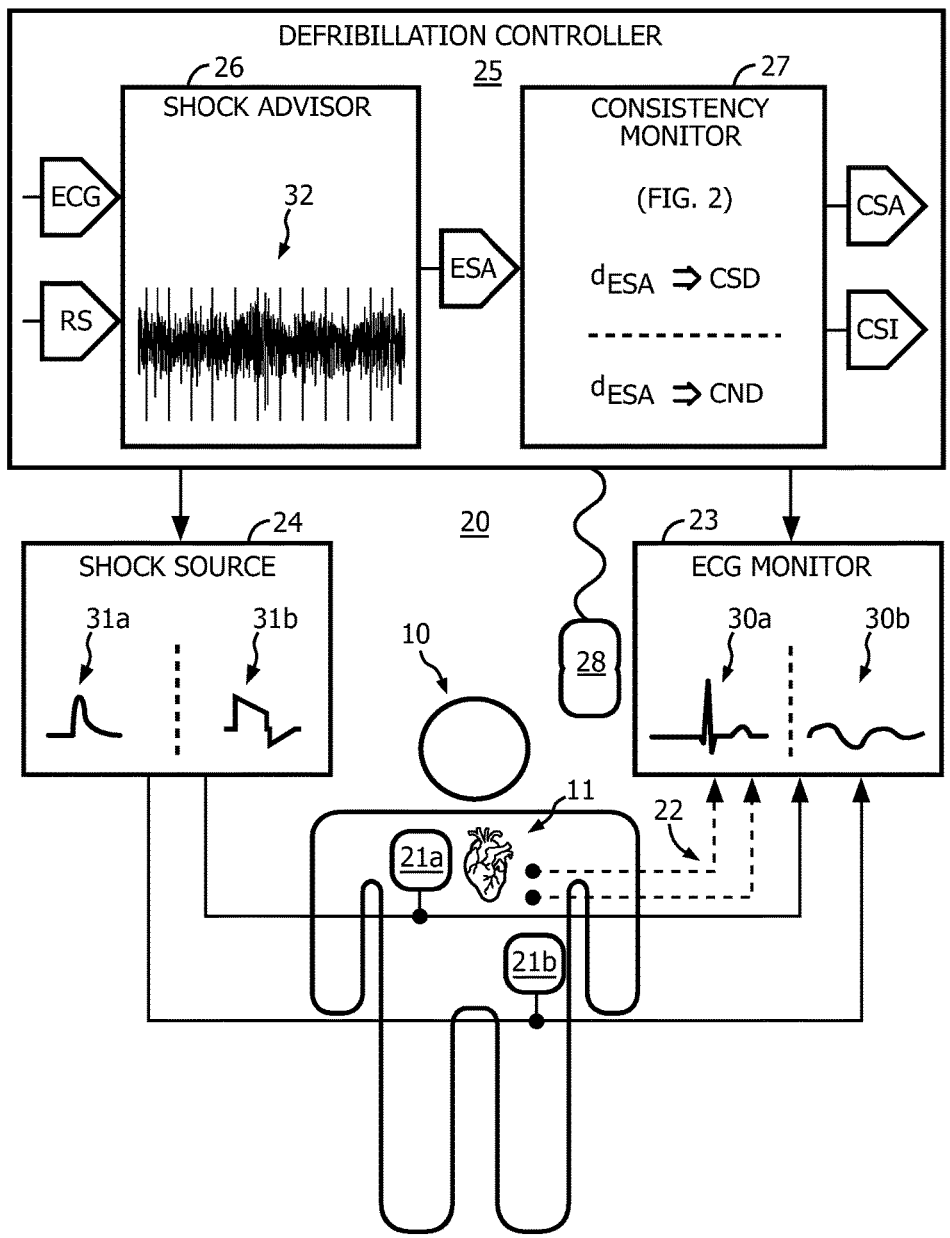
FIG. 1 illustrates an exemplary embodiment of a patient monitoring device in accordance with the present invention.

Referring to FIG. 1, an exemplary embodiment of a patient monitoring device 20 in accordance with the present invention is a defibrillator which employs a pair of electrode pads/paddles 21, optional ECG leads 22, an ECG monitor 23 (internal or external), a shock source 24, a patient monitoring device controller 25, being a defibrillation controller in this exemplary embodiment, and an optional compression pad 28.

Electrode pads/paddles 21 are structurally configured to be conductively applied to a patient 10 in an anterior-apex arrangement as shown in FIG. 1 or in an anterior-posterior arrangement (not shown). Electrode pads/paddles 21 conduct a defibrillation shock from shock source 24 to a heart 11 of patient 10 as controlled by controller 25, and conduct electrical activity of heart 11 of patient 10 to ECG monitor 23. Alternatively or concurrently, ECG leads 22 can be connected to patient 10 to conduct the electrical activity of heart 11 of patient 10 to ECG monitor 23.

ECG monitor 23 is structurally configured to measure an ECG waveform 30 of heart 11 of patient 10 as an indication patient 10 is experiencing an organized heartbeat condition or an unorganized heartbeat condition. As one having ordinary skill in the art shall appreciate in view of the teachings provided herein, an example of ECG waveform 30 indicating an organized heartbeat condition is an ECG waveform 30a without a P-wave that is representative of an organized contraction of the ventricles of heart 11 being capable of pumping blood. An example of ECG waveform 30 indicating patient 10 is experiencing an unorganized heartbeat conditions is a random ECG waveform 30b having zero (0) discernible waves representative of no organized heartbeat activity of heart 11 of patient 10.

In an exemplary embodiment of the present invention, ECG monitor 23 employs a digital signal processor (not shown) for streaming ECG waveform data to defibrillation controller 25.

Shock source 24 is structurally configured to store electric energy for delivery of a defibrillation shock 31 via electrode pads/paddles 21 to heart 11 of patient 10 as controlled by defibrillation controller 25. In practice, defibrillation shock 31 can have any waveform known in the art. Examples of such waveforms include, but are not limited to, a monophasic sinusoidal waveform (positive sine wave) 31a and a biphasic truncated waveform 31b as shown in FIG. 1, for example.

In accordance with exemplary embodiments of the present invention, shock source 24 employs a high voltage capacitor bank (not shown) for storing a high voltage via a high voltage charger and a power supply upon a pressing of a charge button. Shock source 24 further employs a switching/isolation circuit (not shown) for selectively applying a specific waveform of an electric energy charge from the high voltage capacitor bank to electrode pads/paddles 21 as controlled by defibrillation controller 25.

Also in accordance with exemplary embodiments of the present invention, defibrillation controller 25 is structurally configured with hardware, software, firmware and circuitry responsive to the ECG waveform from ECG monitor 23 to control shock source 24 in delivering defibrillation shock 31 via electrode pads/paddles 21 to heart 11 of patient 10 in accordance with one or more shock therapies (e.g., synchronized cardioversion).

To this end, exemplary embodiments of the present invention incorporates modules 26 and 27 within defibrillation controller 25 for executing a process as illustrated in flowchart 40 (FIG. 2) representative of a consistency shock monitoring method in accordance with exemplary embodiments of the present invention for communicating shock advisory decisions to a user of defibrillator 25 in a consistent and accurate manner.

Still referring to FIG. 1, shock advisor 26 executes technique(s) as should be appreciated by one having ordinary skill in the art in view of the teachings provided herein for generating ECG shock advisories ESA from an analysis of ECG waveform 30. Specifically, in operation, shock advisor 26 segments ECG waveform 30 into a time series 32 of ECG segments and for each ECG segment, generates an ECG shock advisory ESA between a shock decision and a non-shock decision.

In practice, shock advisor 26 can utilize virtually any time period for the segmentation of the ECG waveform (e.g., 4.5 seconds per ECG segment), the segmentation time period can be fixed or variable, and the time series can be continuous or intermittent. Also in practice, ECG shock advisories ESA can be additionally decided as one or more intermediate decisions. For example, a ECG shock advisory ESA can either be a shock decision, a non-shock decision or a shock indecision.

Consistency monitor 27 executes techniques in accordance with exemplary embodiments of the present invention for monitoring the consistency of ECG shock advisories ESA between consistent shock decisions and consistent no-shock decisions. Specifically, consistency monitor 27 defines a decision vector $d_{ESA}$ of up to X ECG shock advisory ESA, X≥2, and determines if the decision vector $d_{ESA}$ is indicating consistent shock decisions or consistent no-shock decisions by shock advisor 26.

In practice, for additional ECG shock advisories ESA between a shock decision and a non-shock decision, consistency monitor 27 further determines if the decision vector $d_{ESA}$ is indicating a consistency between consistent shock decisions and consistent no-shock decisions. For example, for shock indecisions, decision vector $d_{ESA}$ can indicate inconsistent shock decisions.

Figure 2:
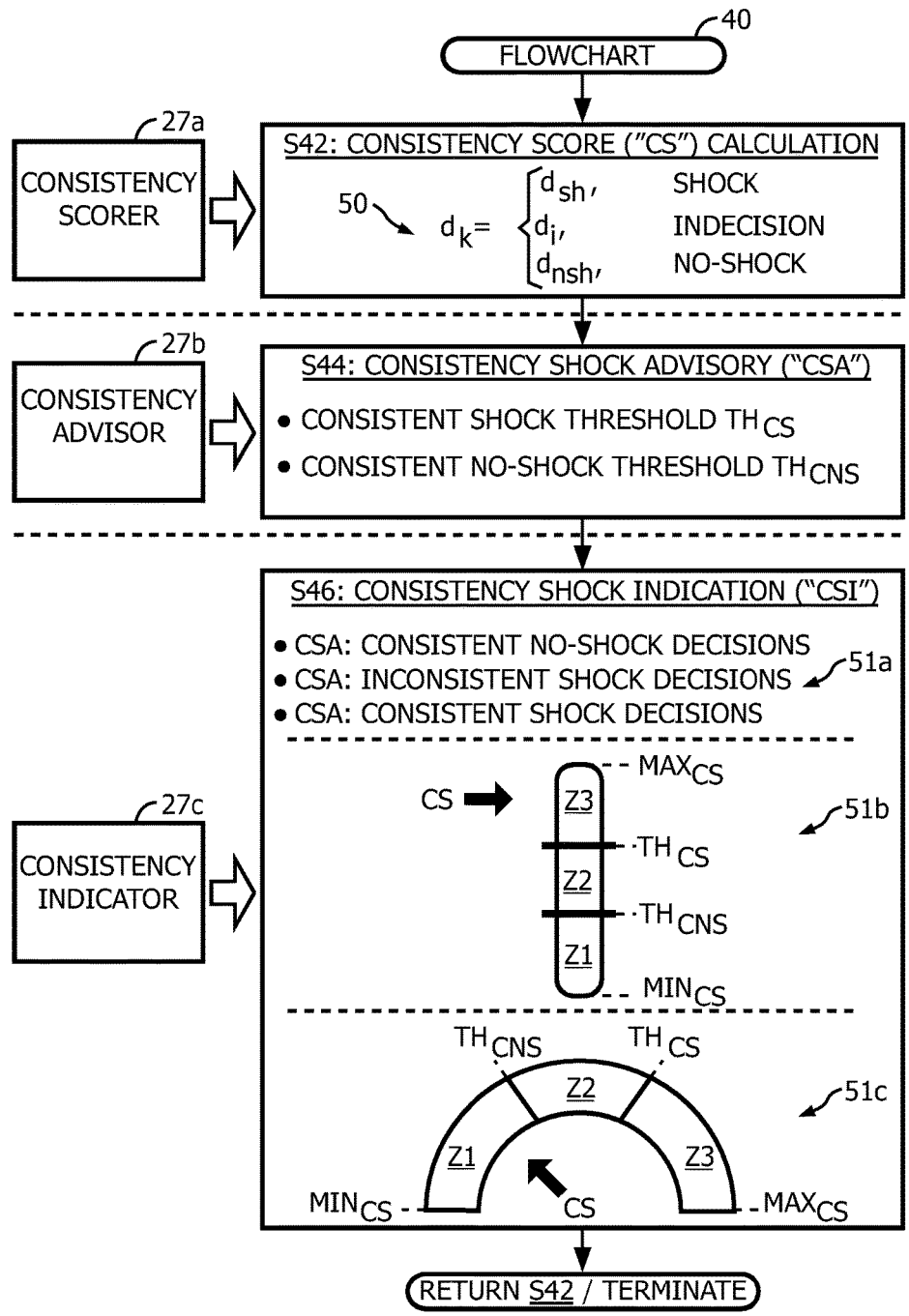
FIG. 2 illustrates a flowchart representative of an exemplary embodiment of consistency shock monitoring method in accordance with the present invention.

To facilitate a further understanding of consistency monitor 27, FIG. 2 illustrates an exemplary embodiment in accordance with the present invention of consistency monitor 27 employing a consistency scorer 27a, a consistency advisor 27b and a consistency indicator 27c executing a flowchart 40 representative of an exemplary consistent shock monitoring method of the present invention. While flowchart 40 is described in the context of each ECG shock advisory ESA by shock advisor 26 being either a shock decision, a non-shock decision or a shock indecision, those having ordinary skill in the art will appreciate in view of the teachings provided herein how to apply the principles of flowchart 40 to any number of possible ECG shock advisories ESA inclusive of shock decisions and non-shock decisions.

Still referring to FIG. 2, in accordance with exemplary embodiments of the present invention, a stage S42 of flowchart 40 encompasses consistency scorer 27a calculating a consistency score CS as a function of each ECG shock advisory within decision vector $d_{ESA}$. To this end, consistency scorer 27a utilizes a scoring profile of a decision score for each ECG shock advisory within decision vector $d_{ESA}$ as a basis for calculating consistency score CS. For example, as shown in FIG. 2, consistency scorer 27a can utilize a scoring profile 50 of a decision score $d_k$. For a shock decision, decision score $d_k$ equals a shock decision score $d_{sh}$. For a shock indecision, decision score $d_k$ equals an shock indecision score $d_i$. For a no-shock advisory decision, decision score $d_k$ equals a non-shock decision score $d_n$.

In an exemplary embodiment of consistency scorer 27a utilizing scoring profile 50, consistency score CS is calculated in accordance with the following equation [1]:

$$CS = Y(D - d_i W)/((d_{sh} - d_i)W) \quad [1]$$

wherein Y is a variable limiting consistency score CS within a minimum/maximum consistency score range $MIN_{CS}/MAX_{CS}$; W is a total weight vector calculated in accordance with the following equation [2]; and D is a weighted sum of ECG shock advisories in accordance with the following equation [3]:

$$W = \Sigma_{k=a}^{N} w_k \quad [2]$$

$$D = \Sigma_{k=a}^{N} w_k d_k \quad [3]$$

where N is the index of latest ECG shocking advisories; a=1 if N<X; a=N−(X−1) if N≥X; and w is a weighted vector.

Still referring to FIG. 2, a stage S44 of flowchart 40 encompasses consistency advisor 27b comparing the calculated consistency score CS of stage S42 to a consistent shock threshold $TH_{CS}$ and a consistent no-shock threshold $TH_{CNS}$ as a basis for generating a consistency shock advisory ("CSA"). In accordance with exemplary embodiments of the present invention, consistency advisor 27b defines consistency zones relative to the aforementioned thresholds as exemplarily shown in the following TABLE 1:

TABLE 1

| CONSISTENCY SCORE ZONE | CONSISTENCY DECISION |
| --- | --- |
| ZONE 1 ("Z1"): −Y ≤ CS ≤ $TH_{CNS}$ | CONSISTENT NO-SHOCK DECISIONS |
| ZONE 2 ("Z2"): $TH_{CNS}$ < CS < $TH_{CS}$ | INCONSISTENT SHOCK DECISIONS |
| ZONE 3 ("Z3"): $TH_{CS}$ ≤ CS ≤ +Y | CONSISTENT SHOCK DECISIONS |

Still referring to FIG. 2, a stage S46 of flowchart 40 encompasses consistency indicator 27c communicating an indication, visual and/or audible, of the consistency shock advisory of stage S44 to a user of defibrillator 20 to facilitate the user in reacting to the ECG shock advisories. Specifically, in operation in accordance with exemplary embodiments of the present invention, consistency indicator 27c generates a visual indicator for display by defibrillator 20 (FIG. 1). In practice, the indicator can take any form (e.g., visual, audible and/or tactile) suitable for timely and accurately communicating the consistency shock advisory to the user of defibrillator 20.

In accordance with an exemplary embodiment of the present invention, consistency indicator 27c controls a display of one of three (3) consistency statements 51a as shown in FIG. 2 that corresponds to the consistency shock advisory CSA of stage S44.

In another exemplary embodiment of the present invention, consistency indicator 27c controls a display of a graphical meter 51b as shown in FIG. 2 having a maximum consistency score $MAX_{CS}$ and a minimum consistency score $MIN_{CS}$ whereby a pointer indicates the consistency score within the consistency zone corresponding to the consistency shock advisory CSA.

In yet another exemplary embodiment of the present invention, consistency indicator 27c controls a display of a graphical meter 51c as shown in FIG. 2 also having a maximum consistency score $MAX_{CS}$ and a minimum consistency score $MIN_{CS}$ whereby a pointer again indicates the consistency score within the consistency zone corresponding to the consistency shock advisory CSA.

Flowchart 40 continually loops through stages S42-S44 for each ECG shock advisory communicated to consistency scorer 27a by shock advisor 26 (FIG. 1).

Figure 3A:
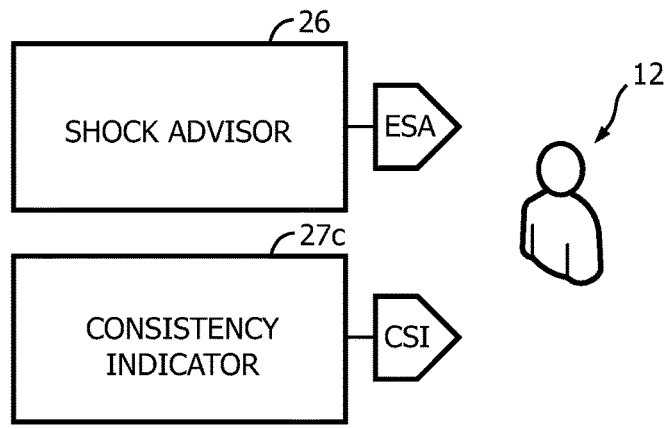
FIG. 3A illustrates a first exemplary embodiment of a consistent shock advisory communication in accordance with the present invention.
Figure 3B:
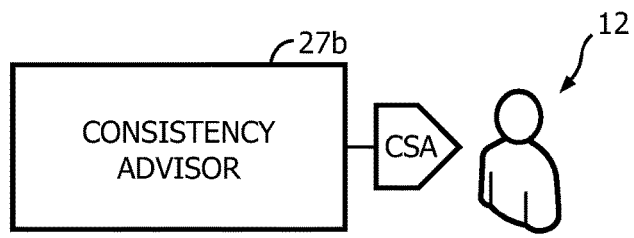
FIG. 3B illustrates a second exemplary embodiment of a consistent shock advisory communication in accordance with the present invention.
Figure 3C:
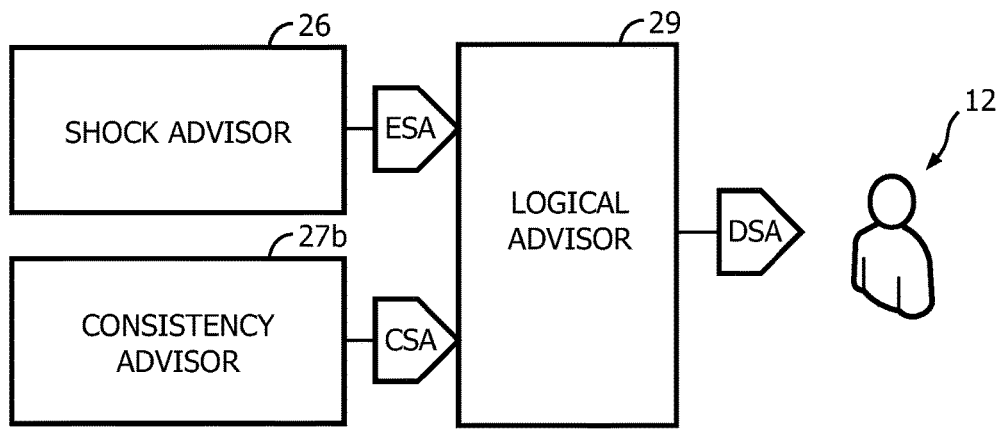
FIG. 3C illustrates a third exemplary embodiment of a consistent shock advisory communication in accordance with the present invention.

FIGS. 3A-3C symbolically shows various communication modes of consistent shock advisories CSA to a user 12 of defibrillator 20 (FIG. 1) via communication components of a defibrillator (e.g., speakers, displays) that one having ordinary skill in the art should appreciate in view of the teachings provided herein. Specifically, for flowchart 40, FIG. 3A symbolically shows a communication mode involving shock advisor 26 (FIG. 1) communicating ECG shock advisories ESA to user 12 and consistency indicator 27c (FIG. 2) communicating a consistency shock indication CSI of stage S44 (FIG. 2) to user 12. Consistency shock indication CSI facilitates a more accurate reaction by user 12 to ECG shock advisories ESA.

Alternatively, omitting stage S46 from flowchart 40 (FIG. 2), FIG. 3B symbolically shows a communication mode involving consistency advisor 27b (FIG. 2) communicating a consistency shock advisory CSA to user 12 as a shock decision, a no-shock decision or any intermediate decision (e.g., shock indecision).

Also as an alternative and again omitting stage S46 from flowchart 40, FIG. 3C symbolically shows a communication mode involving a logical advisor 29 logically combining ECG shock advisories ESA from shock advisor 26 and consistency shock advisories CSA from consistency advisor 27b to generate and communicate a defibrillation shock advisory DSA to user 12 as a shock decision, a no-shock decision or any intermediate decision (e.g., shock indecision).

Figure 4A:
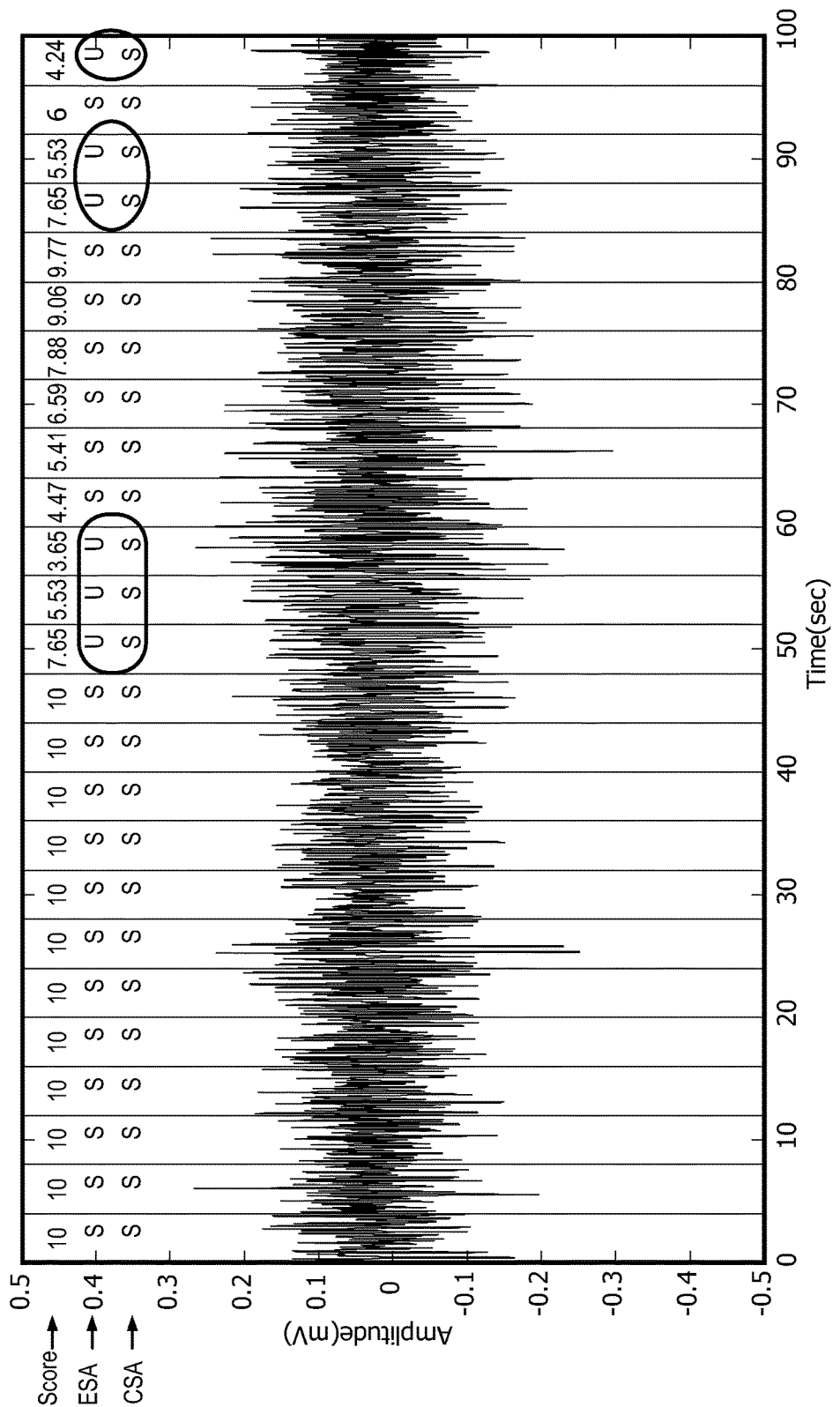
FIG. 4A illustrates a first exemplary consistency scoring of ECG segments having a shockable rhythm.
Figure 4B:
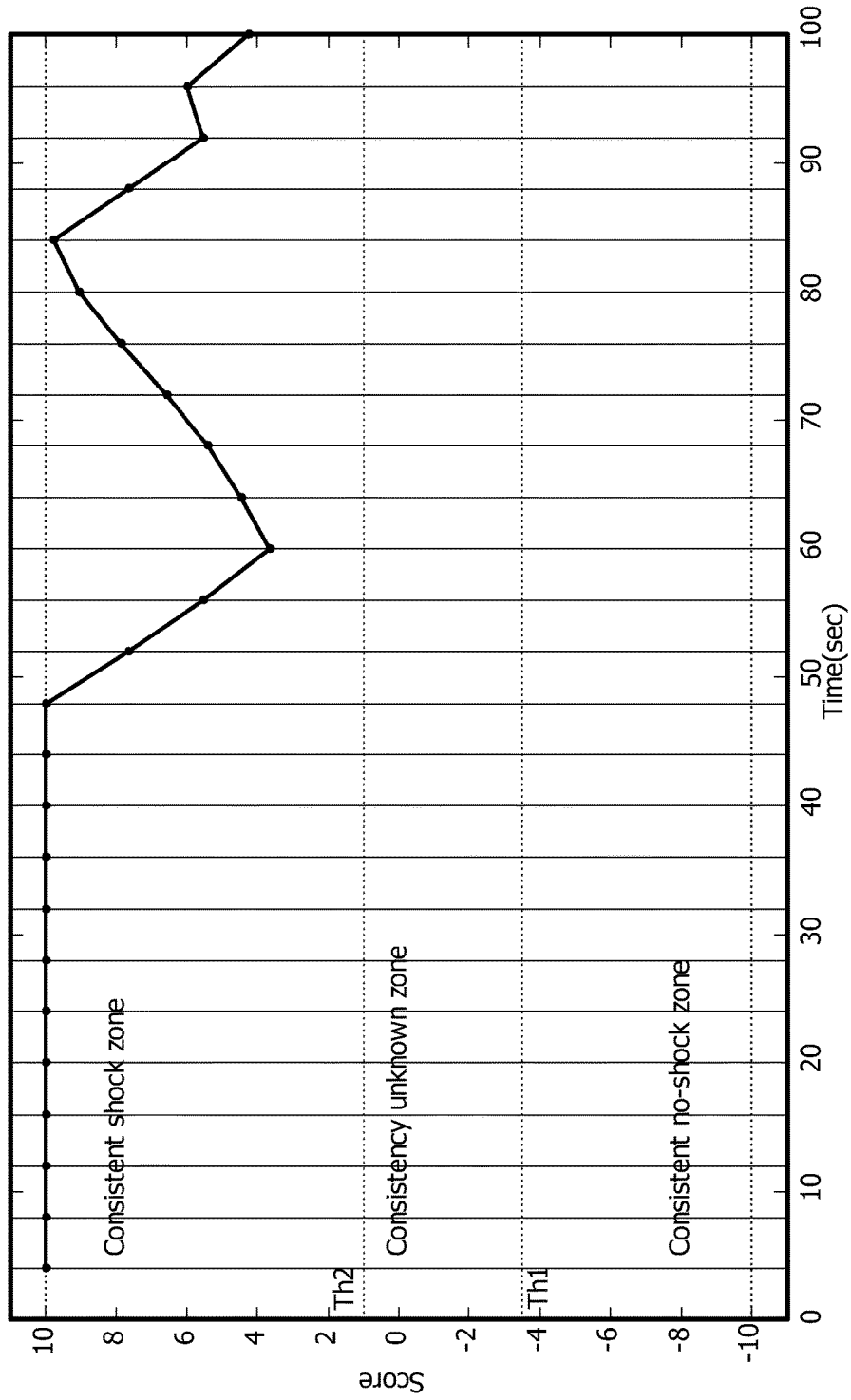
FIG. 4B illustrates a first exemplary consistency scores and decisions of the shock advisory for the ECG segments of FIG. 4A.
Figure 5A:
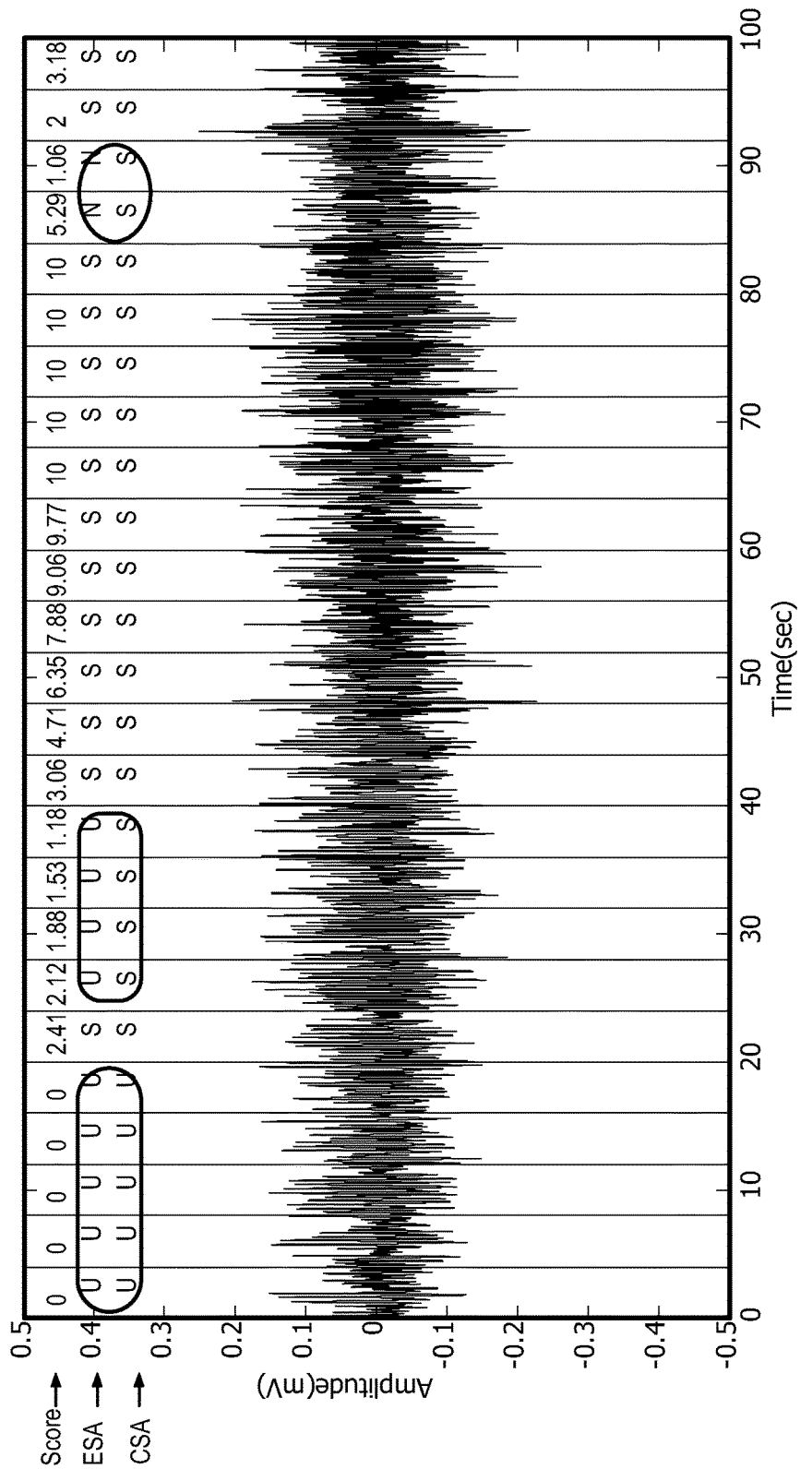
FIG. 5A illustrates a second exemplary consistency scoring of ECG segments having a shockable rhythm.
Figure 5B:
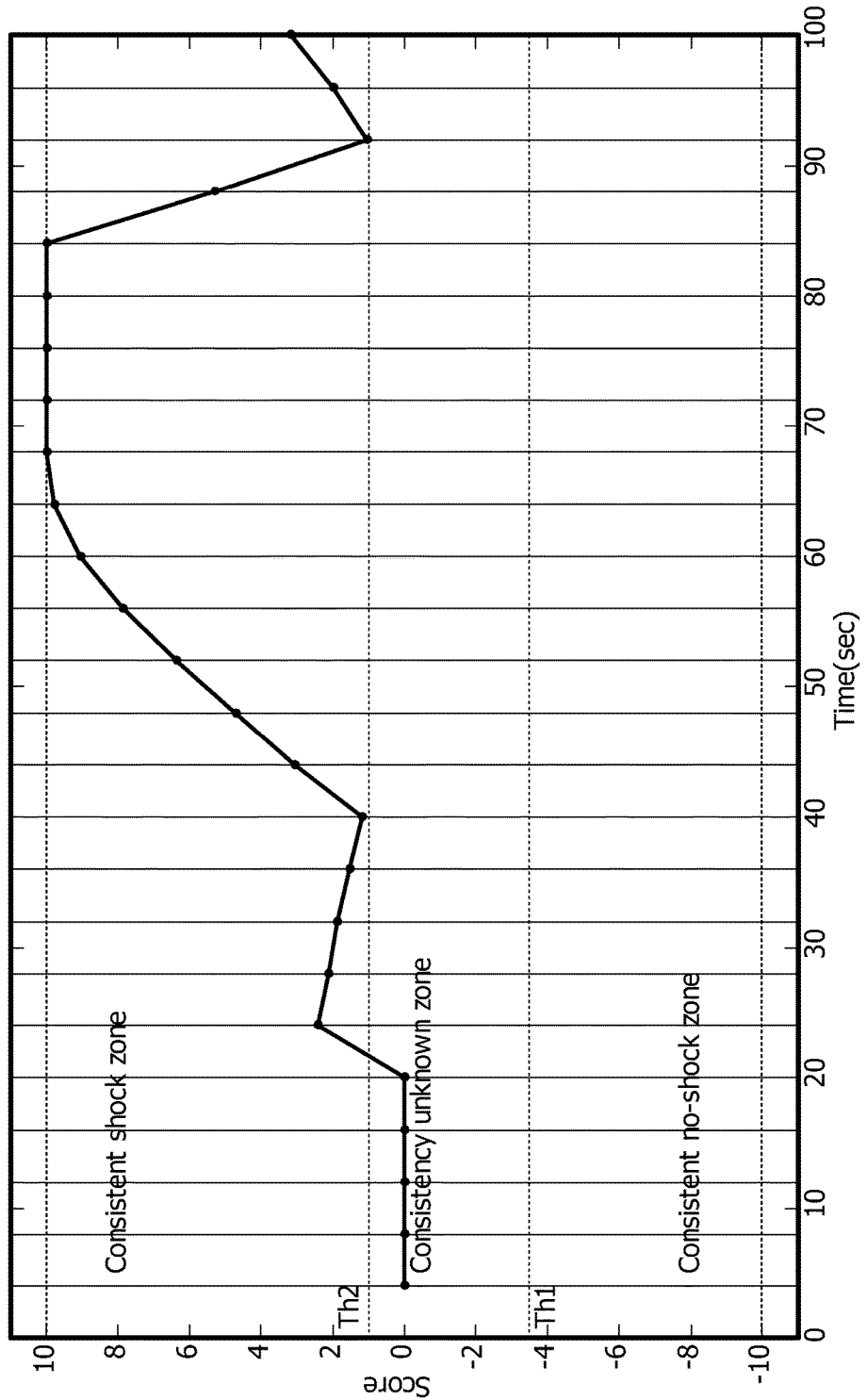
FIG. 5B illustrates a second exemplary consistency scores and decisions of the shock advisory for the ECG segments of FIG. 5A.
Figure 6A:
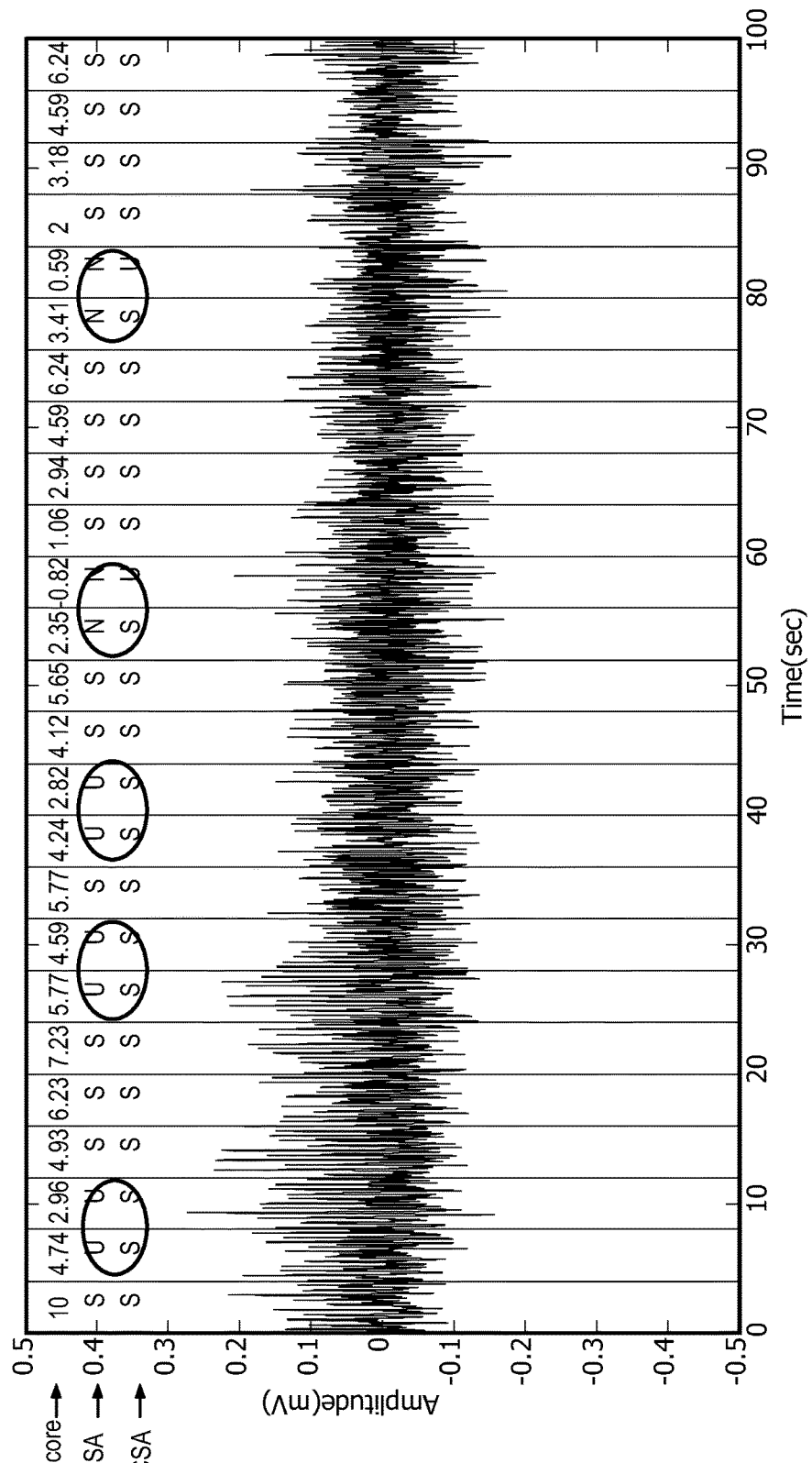
FIG. 6A illustrates a third exemplary consistency scoring of ECG segments having a shockable rhythm.
Figure 6B:
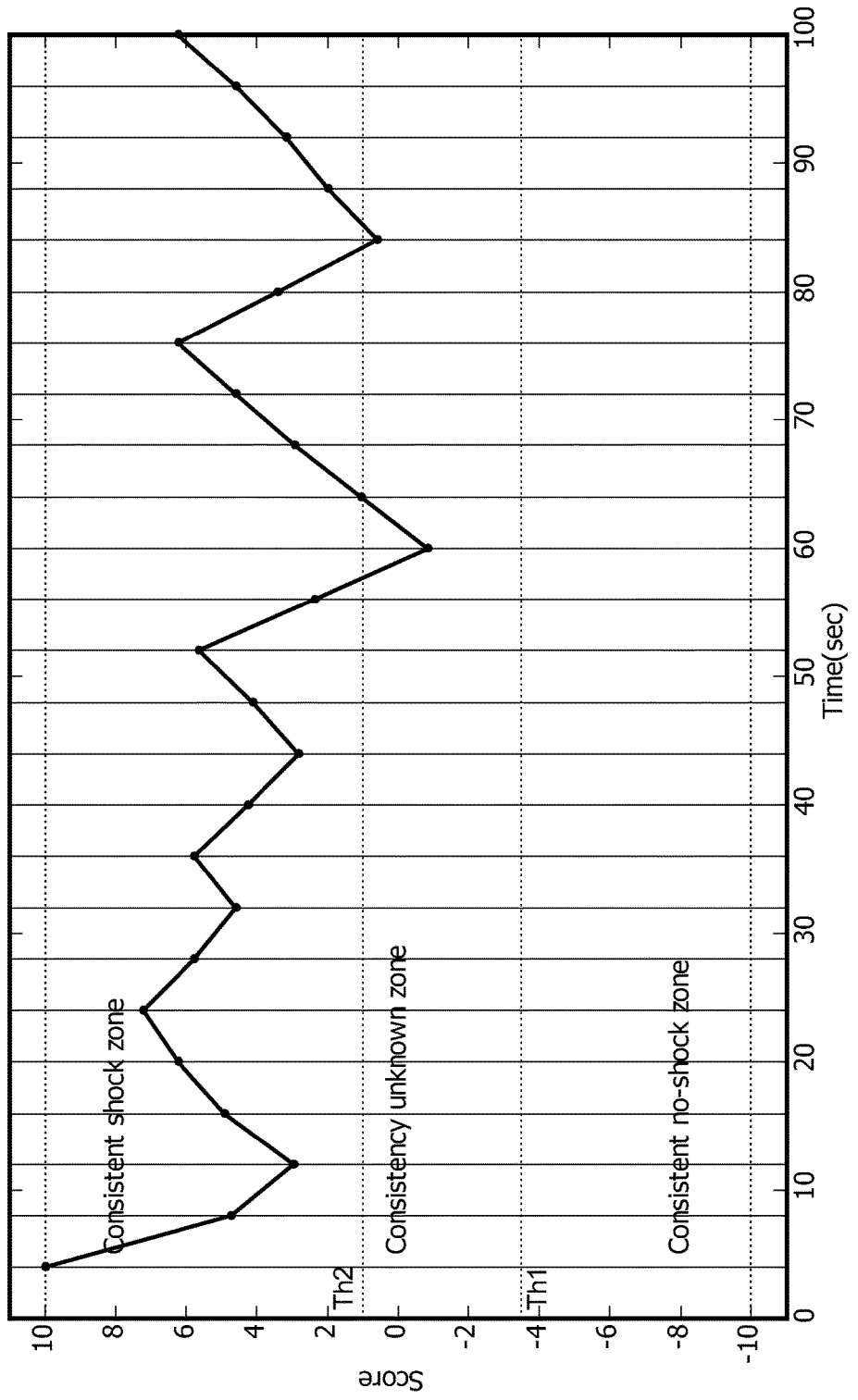
FIG. 6B illustrates a third exemplary consistency scores and decisions of the shock advisory for the ECG segments of FIG. 6A.
Figure 7A:
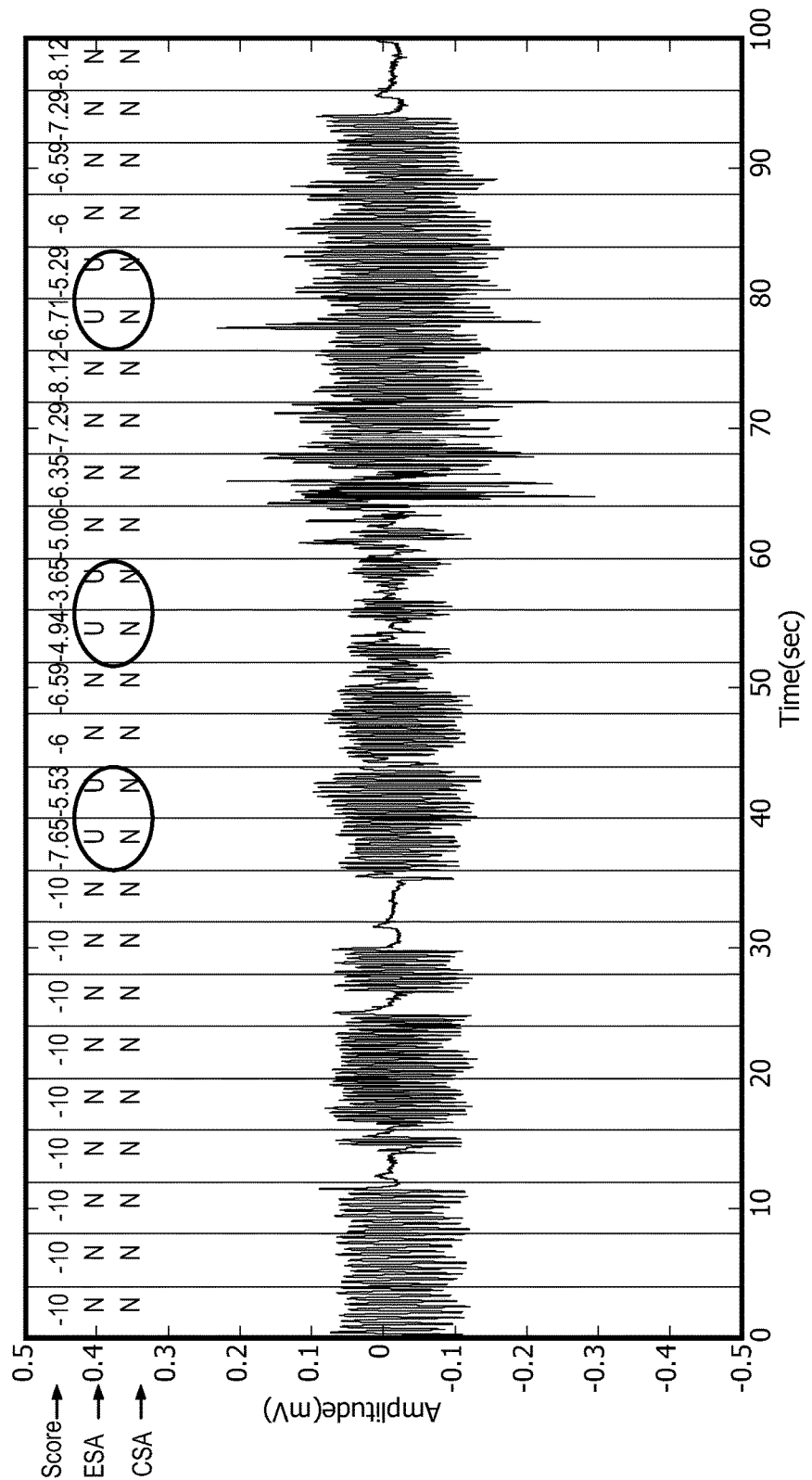
FIG. 7A illustrates a first exemplary consistency scoring of ECG segments having a non-shockable rhythm.
Figure 7B:
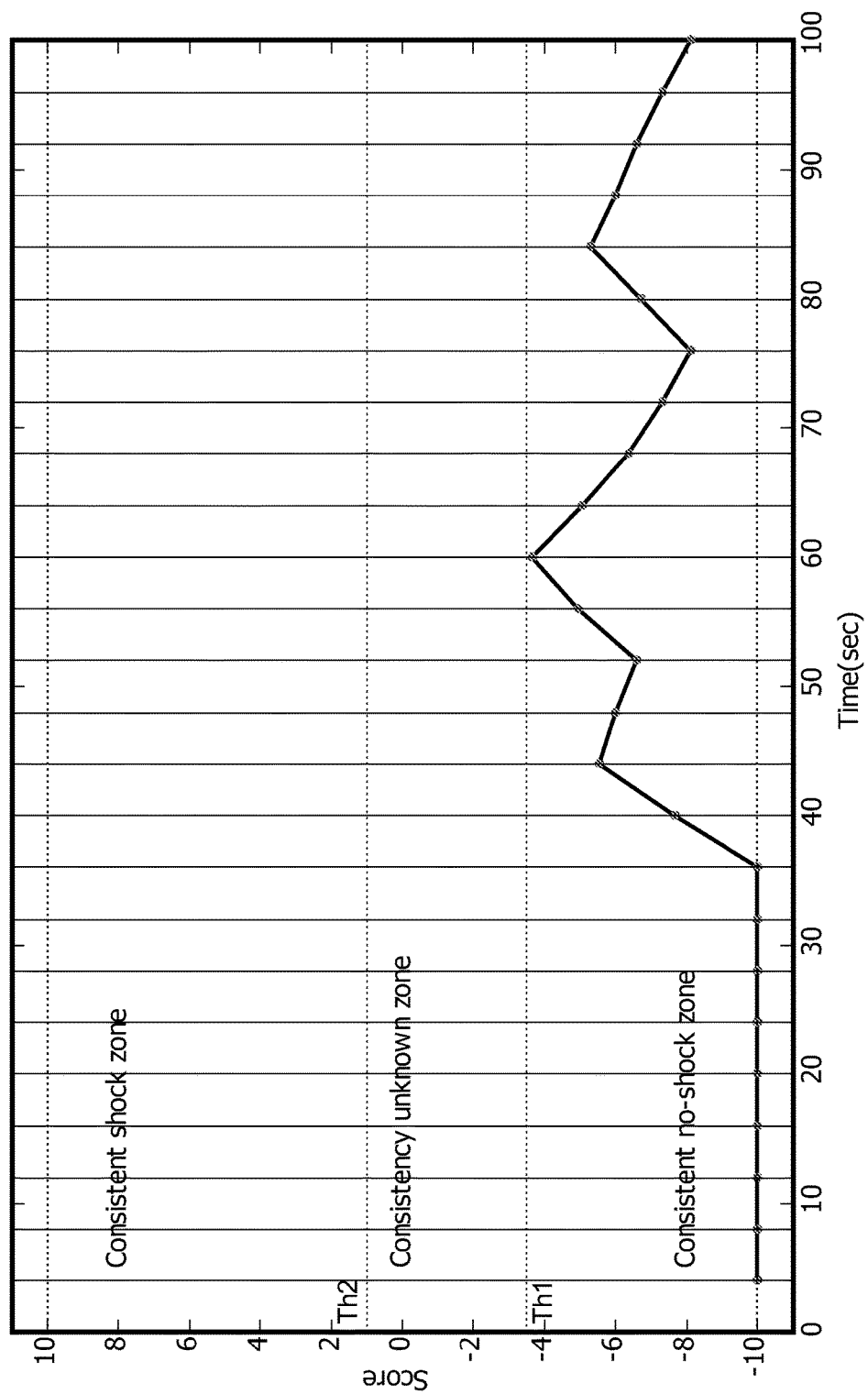
FIG. 7B illustrates a first exemplary consistency scores and decisions of the shock advisory for the ECG segments of FIG. 7A.
Figure 8A:
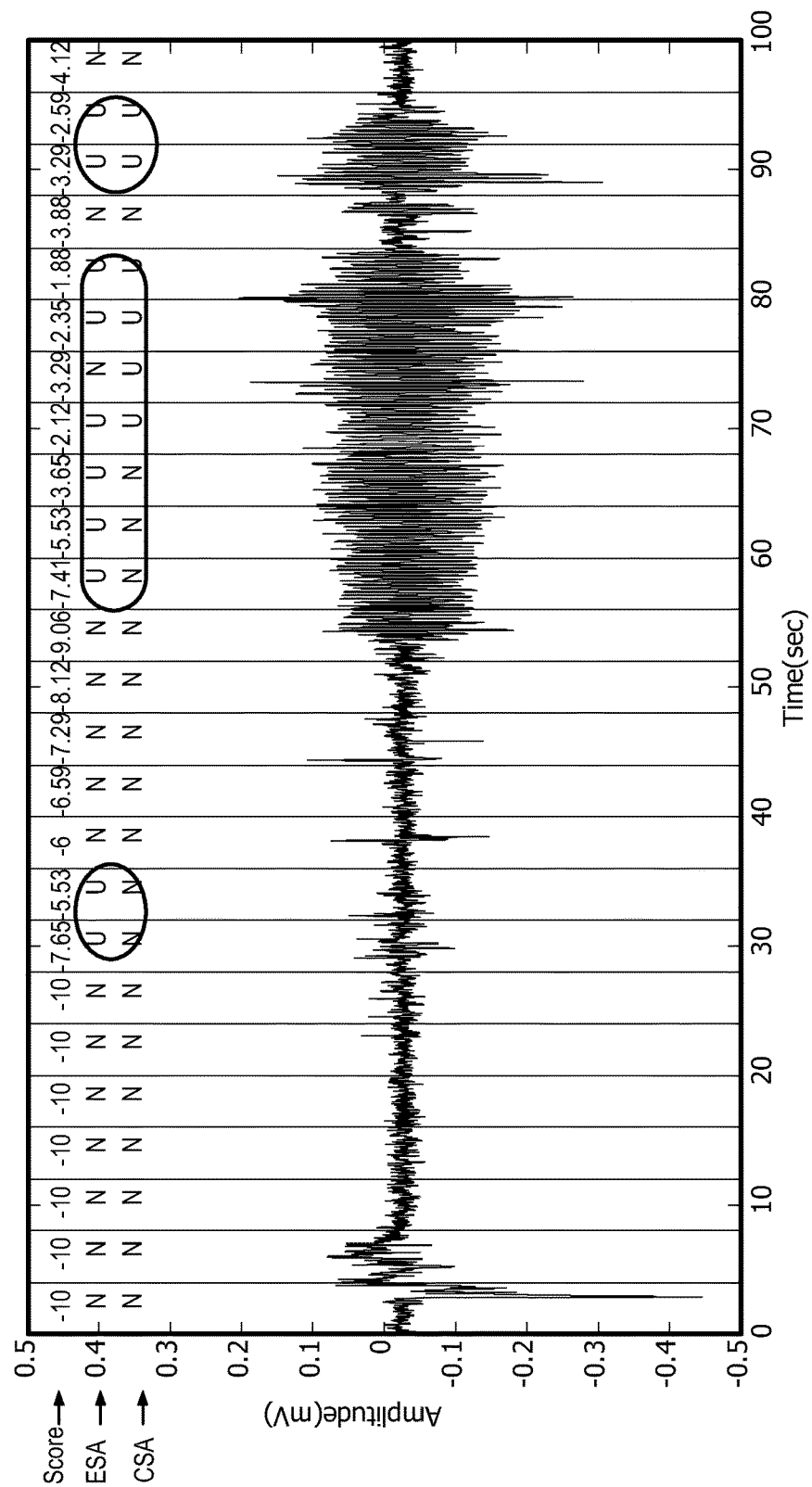
FIG. 8A illustrates a second exemplary consistency scoring of ECG segments having a non-shockable rhythm.
Figure 8B:
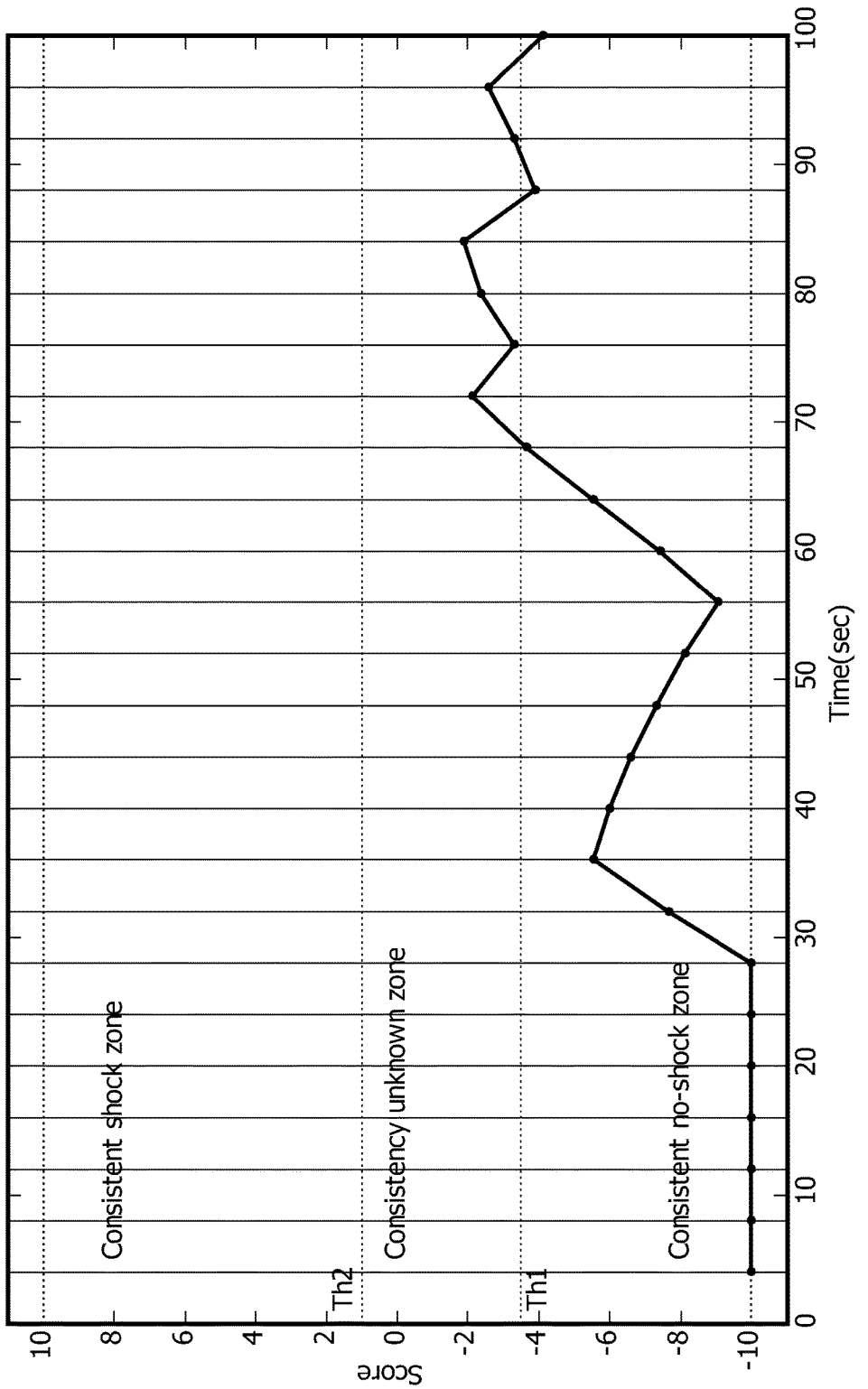
FIG. 8B illustrates a second exemplary consistency scores and decisions of the shock advisory for the ECG segments of FIG. 8A.
Figure 9A:
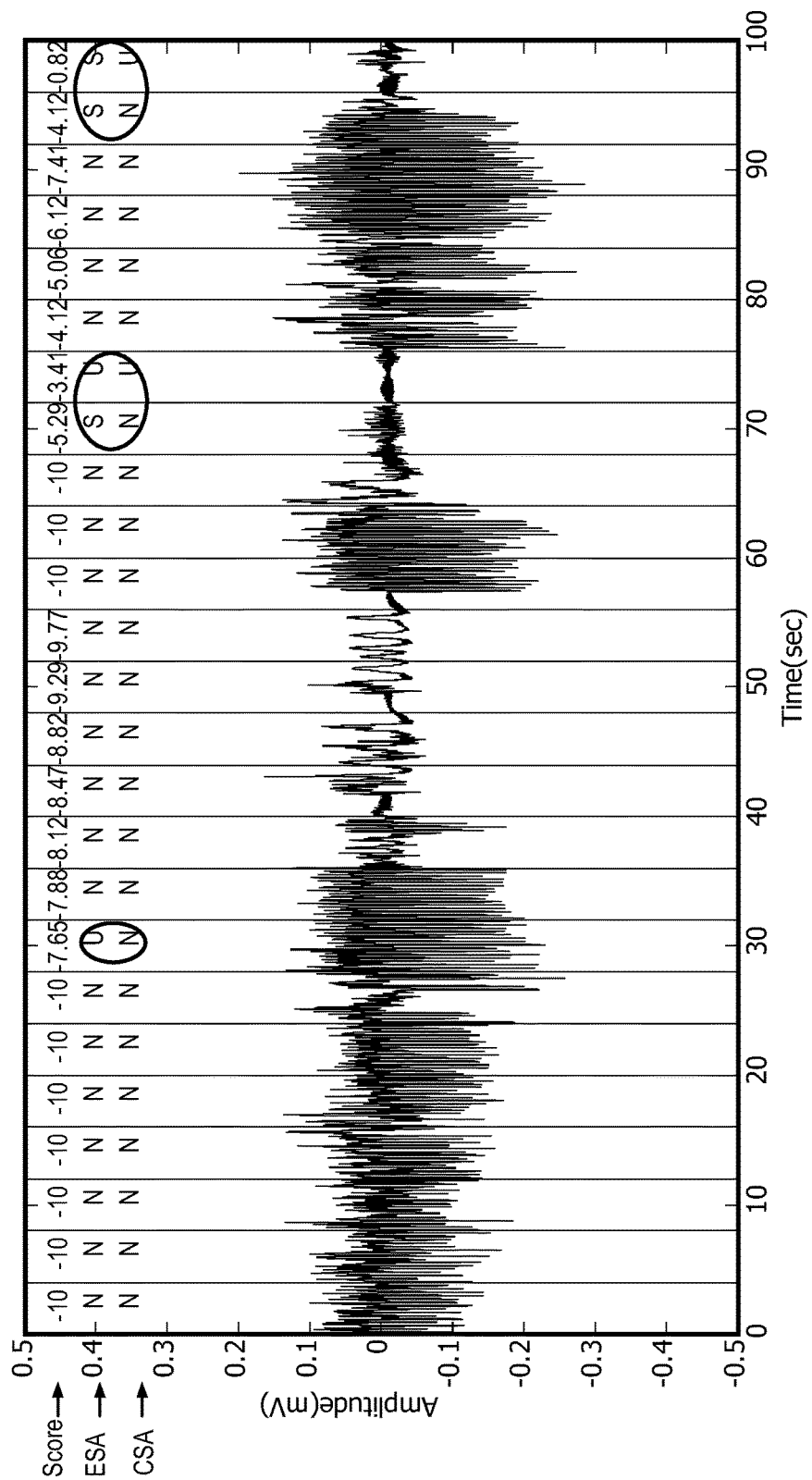
FIG. 9A illustrates a third exemplary consistency scoring of ECG segments having a non-shockable rhythm.
Figure 9B:
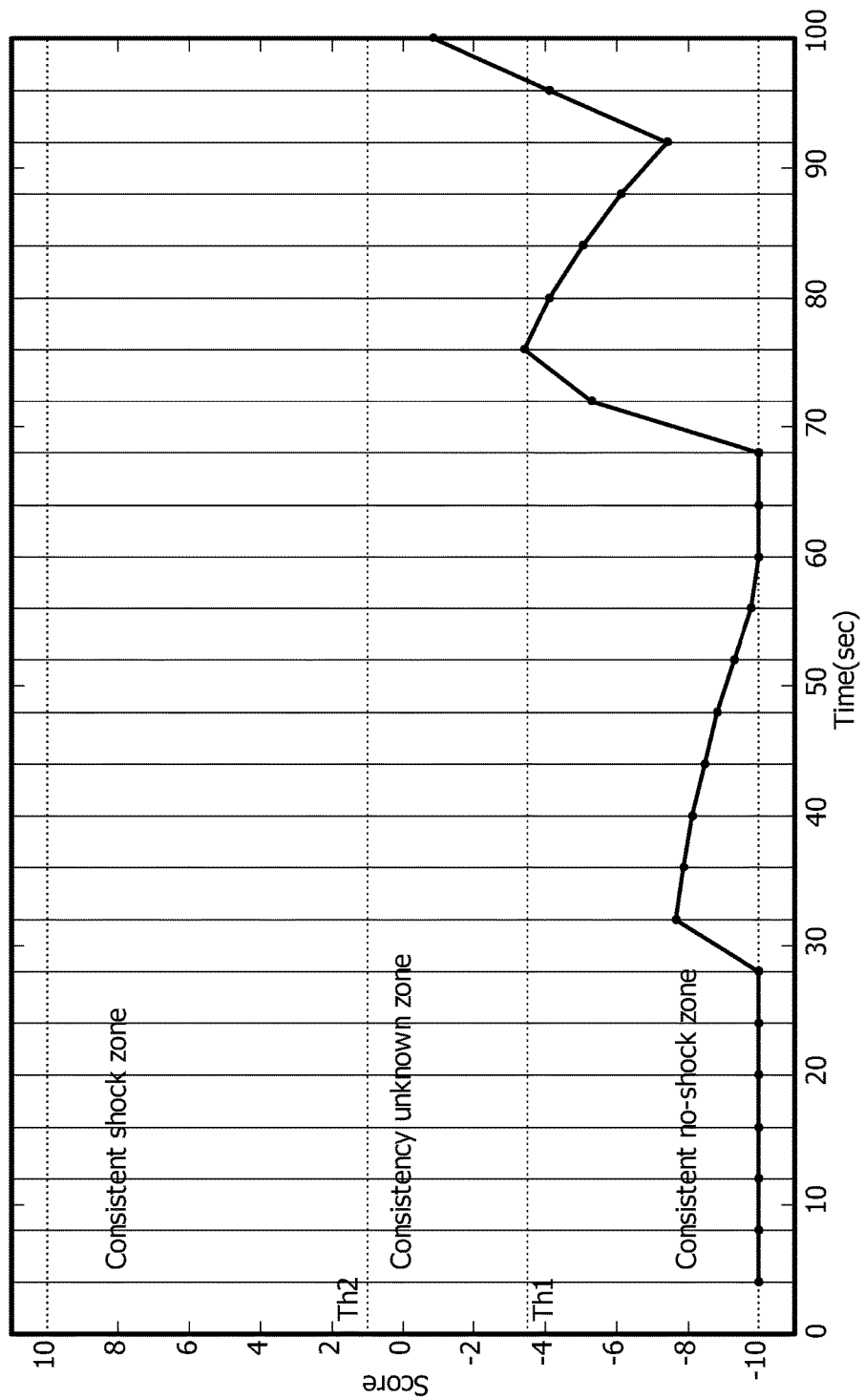
FIG. 9B illustrates a third exemplary consistency scores and decisions of the shock advisory for the ECG segments of FIG. 9A.

FIGS. 4A, 5A and 6A show three (3) exemplary examples of executing stages S42 and S44 of flowchart 40 (FIG. 2) on clinical ECG recordings of shockable rhythms of 100 seconds, and FIGS. 7A, 8A and 9A shows three (3) examples of executing stages S42 and S44 of flowchart 40 on clinical ECG recordings of non-shockable rhythms of 100 seconds. In all these examples, the ECG signal is divided into fixed-length consecutive segments of four (4) seconds.

For each segment at the top of the graphs, FIGS. 4A, 5A, 6A, 7A, 8A and 9A provide a consistency score on a top line, an ECG shock advisory on the middle line and a consistency shock advisory on the bottom line. Segments with 'shock' decisions are marked by '5', 'no-shock' decisions are marked by 'N', and shock indecisions are marked by 'U'. The consistency score is a real number between −10 and 10. The segments with incorrect shock decisions (ECG shock advisory and/or consistency shock advisory) are marked by ovals.

FIGS. 4B, 5B, 6B, 7B, 8B and 9B show the consistency scores of respective FIGS. 4A, 5A, 6A, 7A, 8A and 9A at the end of each segment plotted and compared to the consistent shock threshold and the consistent no-shock threshold to determine whether the consistency score resides in a consistent shock zone, an inconsistent (consistency unknown) zone or a consistent no-shock zone.

As will be appreciated by those having ordinary skill in the art in view of the teachings provided herein, consistency monitor 27 (FIG. 2) used in conjunction with shock advisor 26 (FIG. 2) shows improvement in consistency compared to the individual use of shock advisor 26.

Referring back to FIG. 1, compression pad 28 is structurally configured to be applied to a chest of patient 10 relative to heart 11 for purposes of providing feedback to defibrillation controller 25 as shown or a compression controller (not shown) with the feedback being indicative of the force and rate of a compression motion being applied to the chest of patient 10.

Referring to FIGS. 1-9, those having ordinary skill in the art will appreciate in view of the teachings provided herein numerous benefits of the present invention including, but not limited to, increasing the accuracy of real-time shock advisories, particularly during CPR of sudden cardiac arrest patients.

One having ordinary skill in the art will also appreciate in view of the teachings provided herein that the present invention can be implemented in an Automatic External Defibrillator ("AED"), an Advanced Life Support ("ALS") defibrillator (or ALS defibrillator/monitor), a patient monitor and/or other medical devices having patient monitoring and/or defibrillation functionality.

In addition, while various exemplary embodiments of the present invention have been disclosed, illustrated and described herein, it will be understood by those having ordinary skill in the art in view of the teachings provided herein that such exemplary embodiments of the present invention are illustrative, and that various changes and modifications can be made and equivalents can be substituted for elements thereof without departing from the true scope of the present invention. Further, many modifications can be made to adapt the teachings of the present invention without departing from its central scope. Therefore, it is intended that the present invention not be limited to the particular exemplary embodiments disclosed and described herein as the best mode contemplated for carrying out the present invention, but that the present invention includes all embodiments falling within the scope of the appended claims.

The invention claimed is:

1. A defibrillator, comprising:
   an ECG monitor configured for monitoring an ECG waveform of a heart of a patient; and
   a defibrillation controller operably connected to the ECG monitor to segment the ECG waveform,
   wherein, for each ECG waveform segment of a series of ECG waveform segments, the defibrillation controller generates an ECG shock advisory between a shock decision and a no-shock decision, and
   wherein the defibrillation controller monitors a consistency of the ECG shock advisories between consistent shock decisions and consistent no-shock decisions.

2. The defibrillator of claim 1, wherein each ECG shock advisory is between the shock decision, the no-shock decision and a shock indecision.

3. The defibrillator of claim 2, wherein the consistency of the ECG shock advisories is between consistent shock decisions, consistent no-shock decisions and inconsistent shock decisions.

4. The defibrillator of claim 1, wherein, to monitor the consistency of the ECG shock advisories, the defibrillation controller calculates a consistency score of the ECG shock advisories.

5. The defibrillator of claim 4, wherein, to monitor the consistency of the ECG shock advisories, the defibrillation controller compares the consistency score to at least one of a consistent shock threshold and a consistent no-shock threshold.

6. The defibrillator of claim 5, wherein the defibrillation controller generates a consistency shock advisory responsive to the comparison of the consistency score to at least one of the consistent shock threshold and the consistent no-shock threshold.

7. The defibrillator of claim 6, wherein the defibrillation controller generates a defibrillation shock advisory as a logical combination of the consistency shock advisory and at least one ECG shock advisory.

8. The defibrillator of claim 5, wherein the defibrillation controller generates a consistency shock indication of the comparison of the consistency score to at least one of the consistent shock threshold and the consistent no-shock threshold.

9. The defibrillator of claim 1, wherein the defibrillator is at least one of an automatic external defibrillator or an advanced life support defibrillator.

10. The defibrillator of claim 1, wherein the defibrillator comprises at least one of an automatic external defibrillator, an advanced life support defibrillator or a patient monitor.

11. A defibrillation controller, comprising:
  a shock advisor configured for segmenting an ECG waveform of a heart of a patient into a series of ECG waveform segments, wherein, for each ECG waveform segment of the series of ECG waveform segments, the shock advisor generates an ECG shock advisory between a shock decision and a no-shock decision; and
  a consistency monitor operably connected to the shock advisor and configured to monitor a consistency of the ECG shock advisories between consistent shock decisions and consistent no-shock decisions.

12. The defibrillation controller of claim 11, wherein the ECG shock advisory is between a shock decision, a no-shock decision and a shock indecision.

13. The defibrillation controller of claim 11, wherein the consistency of the ECG shock advisories is between consistent shock decisions, consistent no-shock decisions and inconsistent shock decisions.

14. The defibrillation controller of claim 11, wherein, to monitor the consistency of the ECG shock advisories, the consistency monitor calculates a consistency score of the ECG shock advisories.

15. The defibrillation controller of claim 14, wherein, to monitor the consistency of the ECG shock advisories, the consistency monitor compares the consistency score to at least one of a consistent shock threshold and a consistent no-shock threshold.

16. The defibrillation controller of claim 15, wherein the consistency monitor generates a consistency shock advisory responsive to the comparison of the consistency score to at least one of the consistent shock threshold and the consistent no-shock threshold.

17. The defibrillation controller of claim 15, wherein the consistency monitor generates a consistency shock indication of the comparison of the consistency score to at least one of the consistent shock threshold and the consistent no-shock threshold.

18. A method for shock advisory, comprising:
  segmenting an ECG waveform into a series of ECG waveform segments;
  for each ECG waveform segment of the series of ECG waveform segments, generating an ECG shock advisory between a shock decision and a no-shock decision; and
  monitoring a consistency of the ECG shock advisories between consistent shock decisions and consistent no-shock decisions.

19. The method of claim 18,
  wherein the ECG shock advisory is between a shock decision, a no-shock decision and an shock indecision; and
  wherein the consistency of the ECG shock advisories is between consistent shock decisions, consistent no-shock decisions and inconsistent shock decisions.

20. The method of claim 18,
  wherein monitoring the consistency of the ECG shock advisories includes
    calculating a consistency score of the ECG shock advisories, and
    comparing the consistency score to at least one of a consistent shock threshold or a consistent no-shock threshold; and
  wherein the method further comprises at least one of:
    (i) generating a consistency shock advisory responsive to the comparison of the consistency score to at least one of the consistent shock threshold or the consistent no-shock threshold; or
    (ii) generating a consistency shock indication of the comparison of the consistency score to at least one of the consistent shock threshold or the consistent no-shock threshold.

* * * * *